US007179152B1

(12) United States Patent
Rhoades (10) Patent No.: US 7,179,152 B1
(45) Date of Patent: Feb. 20, 2007

(54) COMPOSITION SUITABLE FOR APPLICATION TO HUMAN SKIN

(75) Inventor: Dean L. Rhoades, Los Angeles, CA (US)

(73) Assignee: DermaNew, Inc., Beverly Hills, CA (US)

( * ) Notice: Subject to any disclaimer, the term of this patent is extended or adjusted under 35 U.S.C. 154(b) by 338 days.

(21) Appl. No.: 10/359,852

(22) Filed: Feb. 7, 2003

(51) Int. Cl.
*A61K 33/08* (2006.01)

(52) U.S. Cl. .............................. 451/41; 451/28; 451/56; 424/401; 424/70.1; 424/489; 514/844

(58) Field of Classification Search ................. 451/28, 451/41, 56; 424/401, 70.1, 70.11, 70.21, 424/78.02, 489, DIG. 5, 70.17; 514/844, 514/846, 873, 952, 975
See application file for complete search history.

(56) References Cited

U.S. PATENT DOCUMENTS

| | | | |
|---|---|---|---|
| 1,653,901 A | 12/1927 | Haessly | |
| 2,985,166 A | 5/1961 | Burkhardt | |
| 3,092,111 A | 6/1963 | Saperstein et al. | |
| 3,852,417 A | 12/1974 | Wdowik | |
| 4,284,533 A | 8/1981 | Imamura et al. | |
| 4,957,747 A | 9/1990 | Stiefel | |
| 4,992,476 A | 2/1991 | Geria | |
| 5,219,571 A | 6/1993 | Wise | |
| 5,360,824 A * | 11/1994 | Barker | 424/680 |
| 5,607,980 A | 3/1997 | McAtee et al. | |
| 5,678,827 A | 10/1997 | Erilli et al. | |
| 5,753,245 A | 5/1998 | Fowler et al. | |
| 5,756,081 A | 5/1998 | Wdowik | |
| 5,800,446 A | 9/1998 | Banuchi | |
| 5,891,449 A * | 4/1999 | Daniel et al. | 424/401 |
| 6,010,268 A | 1/2000 | Sereg et al. | |
| 6,090,085 A | 7/2000 | Mehl, Sr. et al. | |
| 6,139,553 A | 10/2000 | Dotan | |
| 6,290,976 B1 | 9/2001 | Messenger | |
| D477,435 S * | 7/2003 | Angeletta | D28/7 |
| 6,652,888 B2 * | 11/2003 | Rhoades | 424/691 |

(Continued)

FOREIGN PATENT DOCUMENTS

DE 2718158 11/1978

(Continued)

OTHER PUBLICATIONS

Merriam-Webster's Collegiate Dictionary (10th Ed. 1998), pp. 272, 749.

(Continued)

*Primary Examiner*—Lee D. Wilson
*Assistant Examiner*—Anthony Ojini
(74) *Attorney, Agent, or Firm*—Blakely, Sokoloff, Taylor & Zafman, LLP (57) ABSTRACT

An apparatus including an applicator having a first end for mating with a device capable of manipulation by a human hand and a second end having an abrasive surface suitable for contacting areas of human skin, such as, to rejuvenate human skin. There may also be a cushioning layer disposed between the abrasive surface and the end of the applicator it is attached to. A method for manipulating the applicator over an area of human skin to apply the abrasive surface to remove a layer of human skin, with, or without applying a composition to the area of human skin. A composition including abrasive particles in a base.

22 Claims, 8 Drawing Sheets

U.S. PATENT DOCUMENTS

2002/0090385 A1  7/2002  Fox et al.

FOREIGN PATENT DOCUMENTS

| EP | 0336900 | 10/1989 |
| EP | 0571193 A1 | 11/1993 |
| FR | 2565318 A | 11/1985 |
| GB | 1.021.276 | 3/1966 |
| WO | WO 9221306 | 12/1992 |
| WO | WO97/22325 | 6/1997 |
| WO | WO99/21532 | 5/1999 |

OTHER PUBLICATIONS

Epoxy Definitions (2002), www.primeresins.com/onlineresources/epoxy-definitions.php.

The Amer. Heritage Dict. of the English Language (4th Ed. 2000) (online) "moisturizer" (retrieved on Jul. 22, 2003) from the Internet <url:http>//www.bartleby.com/61/4/MO37045.html>.

* cited by examiner

COMPOSITION SUITABLE FOR APPLICATION TO HUMAN SKIN

FIELD

The embodiments disclosed herein relate generally to skin treatment.

BACKGROUND

Facial skin rejuvenation has been accomplished by chemical treatment referred to as "chemical peels" or laser treatment referred to as "laser surgery" and exfoliation by machine driven means, such as with emery paper. Such methods generally require medical supervision and involve some risk of deleterious side effects as well as pain and discomfort during treatment. These methods all require long recovery time between treatments.

Microdermabrasion (e.g., microexfoliation, particle skin resurfacing) is a technique in skin care in which a controlled exfoliation of the skin is performed to improve and remove skin abnormalities. A typical spa microdermabrasion machine consists of a vacuum pump compressor that draws crystals of corundum (aluminum oxide or alumina) from a container through an output tube into a hand piece. When the hand piece is applied to skin it creates a path wherein crystals are drawn across the skin into an suction tube that leads to a disposal container for the used crystals and abraded skin. A filter in the suction tube protects moving parts of the vacuum pump. A technician manipulates the hand piece over the skin of the subject to induce exfoliation.

In addition to the noted facial skin rejuvenation, many individuals seek various treatments to rejuvenate or recondition or otherwise modify their skin, including their face and body. Representative treatments include moisturizing treatments, hair removal and callus reduction or conditioning (e.g., softening), particularly on hands and feet.

DESCRIPTION OF THE DRAWINGS

Various embodiments are illustrated by way of example and not by way of limitation in the figures of the accompanying drawings in which like references indicate similar elements. It should be noted that references to "an," "one," "the," "other," "alternative," or "various" embodiments in this disclosure are not necessarily to the same embodiment, and such references mean at least one.

For example.

DETAILED DESCRIPTION

In the following description, for the purposes of explanation, numerous specific details are set forth in order to provide a thorough understanding of the various embodiments. It will be apparent to one skilled in the art that the embodiments may be practiced without some of these specific details. In other instances, certain structures and devices are omitted or simplified in order to avoid obscuring the details of the various embodiments.

The following description and the accompanying drawings provide examples for the purposes of illustration. However, these examples should not be construed in a limiting sense as they are not intended to provide an exhaustive list of all possible implementations.

The following paragraphs describe embodiments of a composition and device that may be used, in one aspect, in rejuvenating human skin.

In one embodiment, a composition is disclosed including a base and a plurality of abrasive particles. In one embodiment, the composition includes a base including a moisturizer suitable for application to human skin and a plurality of abrasive particles. Suitable abrasive particles include, but are not limited to, inorganic particles such as corundum (e.g., aluminum oxide, alumina, and $Al_2O_3$), silicon carbide, silicon carbide coated particles, magnesium oxide (e.g., MgO), and precious stones including, but not limited to, diamond, garnet, sapphire, ruby, emerald, and topaz. Moreover, an embodiment of the composition can have one or more types of abrasive particles.

In one embodiment, the abrasive particles are microcrystals having an average particle size on the order of 34 microns (µm) to 556 µm (320 to 30 grit). Also, the average particle size of the microcrystals may be on the order of about 42 µm to 198 µm (280 to 60 grit). Representatively, the average particle size of the micro crystals may be on the order of about 60 grit to 80 grit for callus softening.

Embodiments include a composition comprising a base that is capable of suspending the plurality of abrasive particles within the base. In various embodiments, a moisturizer is used as a principal component in the base. Moisturizers are believed to reduce water loss from the skin and draw moisture from inner skin layers up into the outer skin layer. In this regard, the moisturizer can include a substance that attracts moisture to the top skin layer (e.g., a humectant). For example, suitable humectants include glycerin, propylene glycol, alpha hydroxy acids, urea, and lactic acid. The moisturizer may also include substances that tend to reduce water loss by creating a barrier. Such substances include, among others, petrolatum, mineral oil, lanolin and silicone derivatives.

Suitable moisturizers may be used in various forms. For example, liquids such as creams, gels, pastes and emollients may be used. In addition to the moisturizer, the base of the composition may further include antioxidants, aromas/fragrances, vitamins (particularly vitamins A, C and E), emulsifiers, toners, acids (e.g., glycolic acid or salicylic acid), scrubs, serums, lotions, liquids, elixirs, sun screens, neutral gel to suspend the crystals (e.g., a non-moisturizing base), and tonics. Antimicrobial, bactericidal, and thickening agents may also be included in a composition.

Embodiments also include a composition with a liquid base including a cleansing component including, for example, soaps, salicylic acid, and a lauryl sulfate (e.g. sodium lauryl sulfate or sodium laureth sulfate). The cleansing component base may also be combined with a moisturizer. Other components such as surfactants and emulsifiers may further be included.

In an embodiment, abrasive particles of corundum (e.g., alumina) microcrystals are combined with a cream moisturizer base in an amount of about 5 to 100 grams of corundum per ounce of creme, preferably 10 to 50 grams per ounce, and more preferably 10 to 20 grams per ounce. For example, a suitable composition comprises 5 to 75 percent by weight corundum, 5 to 75 percent aloe gel, and 5 to 20 percent sodium lauryl sulfate.

The abrasive nature of the particles in the composition render the composition suitable as a rejuvenator (e.g., exfoliator) to improve the look and feel of an area of human skin and remove skin abnormalities. The abrasive particles dispersed in the composition tend to remove the outer layer of skin (the epidermis) to expose an underlayer of skin. The human body responds by producing a new layer of skin.

With one or more (e.g., a series) of these rejuvenation treatments, the skin subject to the treatment may be improved. Such improvements include improvement in the appearance of fine lines, wrinkles, stretch marks, non-inflammatory acne, acne scars, surgical scars, rough or coarse textured skin, age spots, blotchy skin conditions, and sun damaged skin. In addition, such treatments include rejuvenation of the skin to soften the skin, smooth the skin, sooth the skin. For example, one or more such as the skin of the hands and feet, in improving the appearance and texture of the skin and reducing roughness, rough patches, and callused skin.

In addition to abrasive particles, a composition with a base including a moisturizer tends to condition and moisturize the skin to which it is applied, including cuticles. Suitable additional materials for a composition (e.g., as a portion of the base of the composition) include, for example, safflower, wheat germ, carrot, *calendula* and aloe extracts to sooth and hydrate dry, stressed skin. In addition to a moisturizer, an embodiment of a base may include other additives selected, for instance, for attributes associated with such additives. For example, a base may include peppermint oil to provide invigorating benefits and rose oil to sooth and hydrate dry skin.

Representative compositions include abrasive particles by percentage weight of the composition in the range from 30 percent to 75 percent. In addition, a suitable composition can have a percentage by weight of water in the range of between 20 percent and 50 percent. For example, a composition may include 38 percent by weight aluminum oxide (e.g., corundum crystal), approximately 30 percent by weight water, 4.5 percent by weight caprylic (e.g., capric triglyceride), 3.9 percent by weight ethylhexyl palmitate, 1.9 percent glycerin, 0.9 percent shea butter, 0.9 percent jojoba oil (e.g., *Simmondsia Chinensis* Seed Oil), 3.5 percent by weight safflower (e.g., *Carthamus Tinctorius* Seed Oil), 1.5 percent by weight wheat germ (e.g., *Triticum Vulgare* Oil), 0.2 percent by weight carrot (e.g., *Daucus Carota Sativa* Root Extract), 0.5 percent by weight aloe (e.g., *Aloe Barbadensis* Leaf Juice), 0.2 percent by weight *calendula* (e.g., *Calendula Officinalis* Flower Extract), 0.9 percent by weight peppermint oil, and 0.4 percent by weight rose oil.

Moreover, an embodiment of a composition may include the following ingredients within the following ranges: a range of aluminum oxide or other particle between 30 percent by weight and 42 percent by weight; a range of water between 28 percent by weight and 36 percent by weight; a range of caprylic between 0 percent by weight and 15 percent by weight, a range of ethylhexyl palmitate between 0 percent by weight and 12 percent by weight; a range of glycerin between 0 percent by weight and 5 percent by weight; a range of shea butter between 0 percent by weight and 3 percent by weight; a range of jojoba oil between 0 percent by weight and 3 percent by weight; a range of safflower seed oil between 0 percent by weight and 10 percent by weight; a range of wheat germ between 0 percent by weight and 10 percent by weight; a range of carrot between 0 percent by weight and 2 percent by weight; a range of aloe between 0 percent by weight and 5 percent by weight; a range of *calendula* between 0 percent by weight and 2 percent by weight; a range of peppermint oil between 0 percent by weight and 10 percent by weight; and a range of rose oil between 0 percent by weight and 5 percent by weight. Moreover, embodiments include a range of wheat germ extract between 0 percent by weight and 3 percent by weight and wheat bran extract between 0 percent by weight and 3 percent by weight.

An embodiment suitable in one aspect, for use in a rejuvenation treatment or treatments of the human hand and/or foot such as to soften or minimize calluses includes aluminum oxide having a 100 mesh (large) in a 30 percent to 75 percent by weight concentration, water having a 30.24 percent by weight concentration, 4.5 percent by weight caprylic, 3.9 percent by weight ethylhexyl palmitate, 3.5 percent by weight safflower seed oil, 1.9 percent by weight glycerin, and 0.9 percent by weight jojoba oil.

One example of a suitable composition including corundum (e.g., alumina, aluminum oxide, or $Al_2O_3$) microcrystals and a cream moisturizer (e.g., at approximately 14 grams microcrystals per ounce of cream) includes the components listed below and a range of plus/minus 15 percent of each of the percentages listed:

| Ingredients | Percentage by Weight |
| --- | --- |
| Aluminum Oxide | 38.00 |
| Water (Aqua) | 30.24 |
| Caprylic/Capric Triglyceride | 4.50 |
| Ethylhexyl Palmitate | 3.90 |
| Carthamus Tinctorius (Safflower) Seed Oil | 3.50 |
| Cetearyl Alcohol | 2.50 |
| Sodium Cetearyl Sulfate | 1.90 |
| Glycerin | 1.90 |
| Stearic Acid | 1.50 |
| Triticum Vulgare (Wheat Germ) Oil | 1.50 |
| Propylene Glycol | 1.40 |
| Panthenol | 0.60 |
| Lecithin | 0.50 |
| Cetyl Alcohol | 1.00 |
| Tocopheryl Acetate | 0.15 |
| Retinyl Palmitate | 0.10 |
| Shea Butter | 0.90 |
| Simmondsia Chinensis (Jojoba) Seed Oil | 0.90 |
| Ascorbic Acid | 0.30 |
| Daucus Carota Sativa (Carrot) Root Extract | 0.20 |
| Triticum Vulgare (Wheat) Germ Extract | 0.20 |
| Triticum Vulgare (Wheat) Bran Extract | 0.20 |
| Aminomethyl Propanediol | 0.50 |
| Aloe Barbadensis Leaf Juice | 0.50 |
| Calendula Officinalis Flower Extract | 0.20 |
| Ginkgo Biloba Extract | 0.20 |
| Azulene | 0.20 |
| Phenoxyethanol | 0.50 |
| Methylparaben | 0.20 |

-continued

| Ingredients | Percentage by Weight |
| --- | --- |
| Propylparaben | 0.15 |
| Ethylparaben | 0.10 |
| Butylparaben | 0.10 |
| Isobutylparaben | 0.15 |
| Peppermint Oil | 0.90 |
| Rose Oil | 0.40 |
| FDC Blue 1 | 0.01 |

In addition, a skin rejuvenation composition embodiment may include green tea extract having polyphenols, grape seed extract having flavonoids and polyphenols (specific antioxidant that tends to reduce oxidative stress by neutralizing free radicals) that help protect against the sun ultraviolet (e.g., UVA) rays, bacoclamine having a powerful anti-inflammatory agent (e.g., Ayurvedic herb *bacopa monniera* extract), and oat extract having a soothing anti-inflammatory properties.

For example, one composition for skin rejuvenation including a facial rejuvenation may include the following ingredients: aluminum oxide in a range between 5 percent and 75 percent by weight, water in a range between 30 percent and 40 percent by weight, caprylic in a range between 0 percent and 10 percent by weight, octyl palmitate in a range between 0 percent and 10 percent by weight, safflower seed oil in a range between 0 percent and 10 percent by weight, wheat germ oil in a range between 0 percent and 5 percent by weight, wine extract in a range between 0 percent and 5 percent by weight, *bacopa monniera* extract in a range between 0 percent and 5 percent by weight, PEG-8 in a range between 0 percent and 5 percent by weight, hydroxyethyl cellulose in range between 0 percent and 5 percent by weight, grape seed extract (*vitis vinifera*) in a range between 0 percent and 2 percent by weight, ascorbyl palmitate in a range between 0 percent and 2 percent by weight, hydrolyzed oat flour in a range between 0 percent and 2 percent by weight, carrot seed extract in a range between 0 percent and 2 percent by weight, bisabolol in a range between 0 percent and 5 percent by weight, wheat germ extract in a range between 0 percent and 5 percent by weight, wheat bran extract in a range between 0 percent and 5 percent by weight, green tea leaf extract (*camellia sinensis*) in a range between 0 percent and 5 percent by weight, beta carotene in a range between 0 percent and 7 percent by weight, lavender oil (*lavandula angustifolia*) in a range between 0 percent and 3 percent by weight, geranium oil (*geranium maculatum*) in a range of 0 percent and 4 percent by weight, and ylang ylang oil (*cananga odorata* flower) in a range between 0 percent and 2.5 percent by weight.

Moreover, for example, one composition for skin rejuvenation, including facial rejuvenation may include 30 to 60 percent by weight aluminum oxide, and plus/minus 15 percent of the following example percentages by weight: 34.65 percent by weight (e.g., 29 to 39 percent) water; 3.5 percent by weight caprylic; 3.2 percent by weight octyl palmitate; 3 percent by weight safflower seed oil; 1.2 percent by weight wheat germ oil; 1.2 percent by weight wine extract; 1.1 percent by weight *bacopa monniera* extract; 1 percent by weight PEG-8; 1 percent by weight hydroxyethyl cellulose; 0.1 percent by weight ascorbyl palmitate; 0.1 percent by weight grape seed extract; 0.1 percent by weight hydrolyzed oat flour; 0.1 percent by weight carrot seed extract; 0.25 percent by weight bisabolol; 0.2 percent by weight wheat germ extract; 0.2 percent by weight wheat bran extract; 0.2 percent by weight green tea leaf extract; 0.45 percent by weight beta carotene; 0.3 percent by weight lavender oil; 0.4 percent by weight geranium oil; and 0.35 percent by weight ylang ylang oil. Other suitable compositions may be used as well.

Moreover, a tool or device having an applicator as described herein may apply an embodiment of the compositions described above to smooth and refine the skin by applying a firm, yet gentle pressure, and moving the applicator across the skin with upward circular movement for one to five minutes. For example, a device or tool for manipulating any of the above-mentioned compositions may include one with or without a power source, or for grasping by a human hand, such as those described herein. The tool or device may include a round foam applicator, such as those described in related U.S. Patent Application Publication No. 2001-0018061 A1, entitled "Composition, Apparatus and Method for Rejuvenation," published Aug. 30, 2001, that may be used to apply such a composition.

In one embodiment, the composition is provided in a jar (not shown) (e.g., containing 150 grams of hand and foot cream with abrasives) having a mouth large enough for an applicator of an apparatus (such as described below or in U.S. Patent Application Publication No. 2001-0018061 A1, published Aug. 30, 2001 "Composition, Apparatus and Method for Skin Rejuvenation") to be dipped into the composition in the jar. Alternatively, the composition may be scooped out of the jar by hand and applied to the skin area to be treated. Pump mechanisms or squirt bottle tube configurations for dispensing the compositions are also suitable.

In another embodiment, an apparatus suitable for contacting the skin is disclosed. One embodiment of an apparatus includes a portable apparatus having a moveable head and an applicator coupled to the moveable head. The applicator has dimensions suitable for contacting localized areas of human skin, such as areas of the face, limbs, hands and feet. It is appreciated that the apparatus described herein may be used with or without a composition such as described above.

Figure 1:
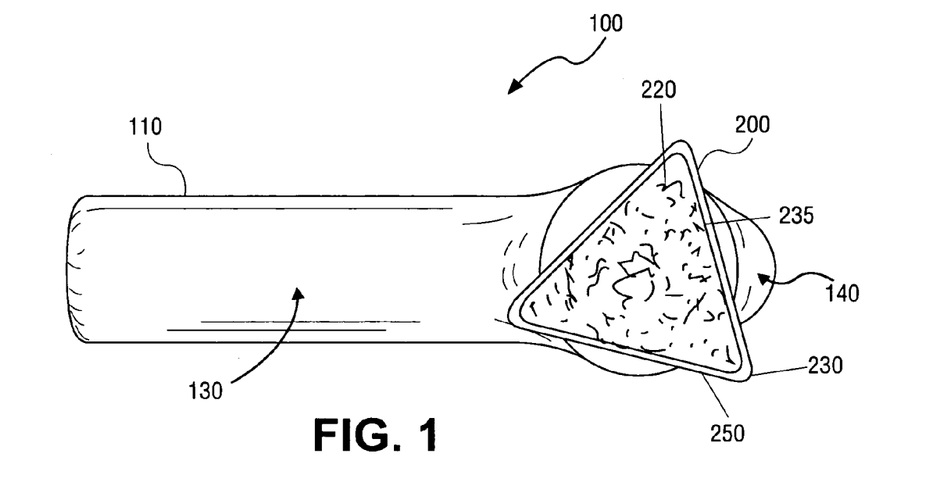
FIG. 1 is a schematic plan view of one embodiment of an apparatus having an applicator coupled to a device.
Figure 2:
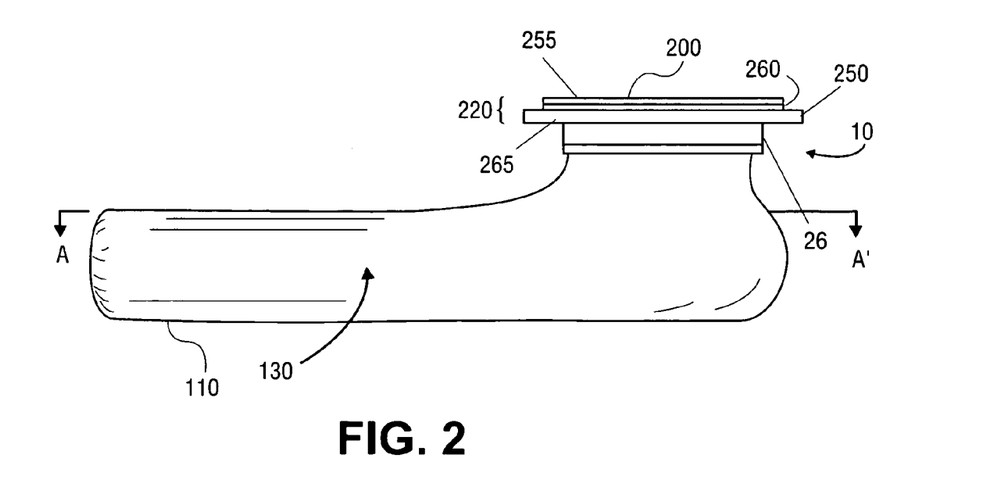
FIG. 2 is a schematic side view of the applicator of FIG. 1.

FIG. 1 is a schematic plan view of one embodiment of an apparatus having an applicator coupled to a device. FIG. 2 is a schematic side view of the applicator of FIG. 1. Referring to the example shown in FIG. 1 and FIG. 2, apparatus 100 includes device or tool 110 and applicator 200. Device or tool 110 may be a static device or tool in the sense that it contains no moveable parts, or a dynamic device or tool in the sense that it includes moveable parts such as a device that vibrates or otherwise moves a portion of device or tool 110. The dynamic device or tool may be powered by fixed or moveable internal power supply such as battery power, or an external source such as a cord connected to a wall outlet. Moreover, device or tool 110 may be powered by a direct current ("DC") battery or by an alternating current ("AC") power source.

Device or tool 110 includes handle portion 130 and head portion 140. Handle portion 130 is capable of manipulation by a human hand and is suitable for gripping by a human hand, for example, with at least one finger of an adult human hand capable of extending around handle portion 130 to contact a thumb of the same hand. In this manner, device or tool 110 is of a size such that it may be maneuvered within a human hand. In one embodiment, handle portion 130 is adapted, at least for a dynamic device, to house in an interior volume, a removable/replaceable power source, such as batteries (e.g., multiple AA batteries), optional circuitry for coupling to an AC power source, and circuitry to operate a motor (e.g., DC) driven apparatus. Device or tool 110, including handle portion 130 and head portion 140, in one embodiment, is formed of a plastic casing.

Figure 3:
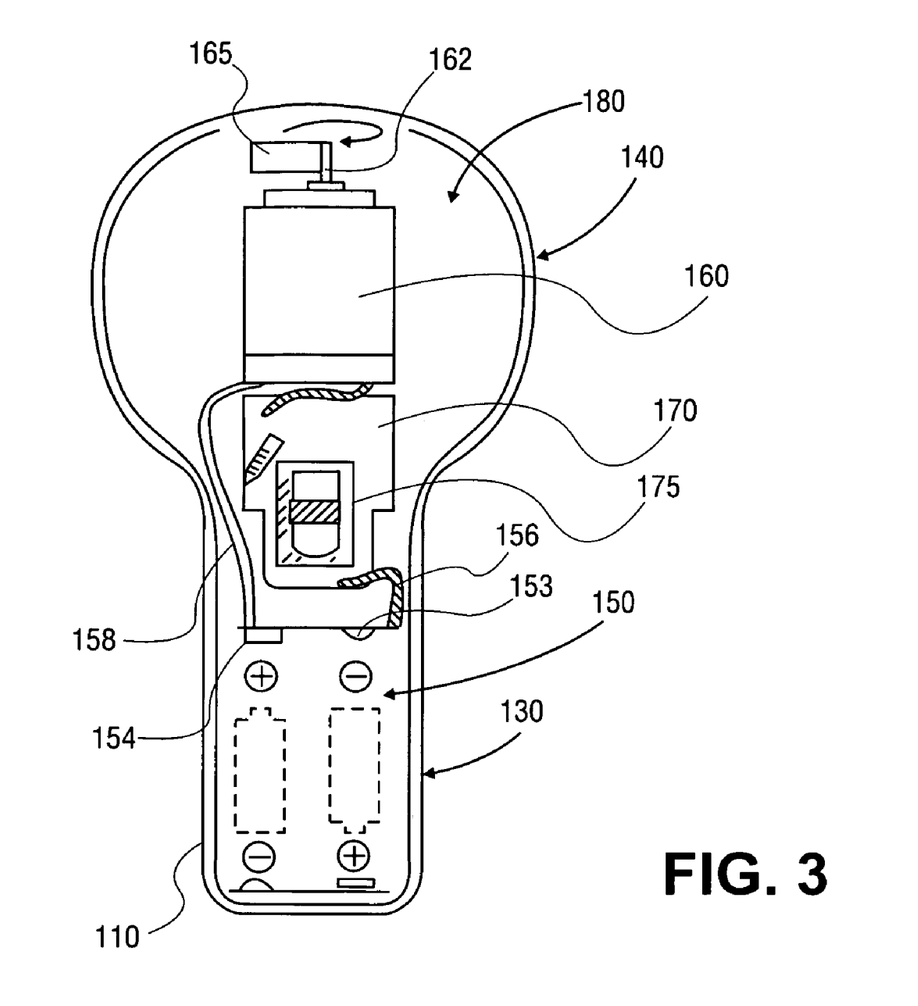
FIG. 3 shows a schematic cross-sectional view of an embodiment of the device or tool through line A—A of FIG. 2.

FIG. 3 shows a schematic cross-sectional view of an embodiment of device or tool 11 through line A—A of FIG. 2, specifically illustrating a dynamic device including, in this embodiment, a mechanism to vibrate head portion 140 of device or tool 110. In this embodiment, device or tool 110 includes handle portion 130 having interior chamber 150 to accommodate a removable power source. In one example, the power source is two AA batteries that fit within interior chamber 150 of handle portion 140. A location of conductors 153 and 154 define an end of the interior chamber 150. Leads 156 and 158 are connected to conductors 153 and 154, respectively, and bring current to/from motor 160. Lead 156 is coupled to circuit board 170 that includes switch 175 to control the operation of motor 160. Switch 175 may be a two-position switch (ON/OFF) or a multiple position switch for operating motor 160 at multiple speeds.

Motor 160 is positioned, in this example, in interior portion 180 of head portion 140 of device or tool 110 and includes shaft 162 extending from one end of motor 160. Shaft 162 is rotated (as illustrated) with the operation of motor 160.

Connected to an end of shaft 162 of motor 160 is eccentric mass 165. In this embodiment, eccentric mass 165 is a semi-cylindrical body coupled at its axis to post 162. In this manner, as eccentric mass 165 rotates, its shape generates a rhythmic motion in head portion 140 of device or tool 110 producing a vibration.

In addition to device or tool 110, the embodiment of apparatus 100, illustrated in FIG. 1 and FIG. 2, applicator 200 includes pad 220 including, in one embodiment, an abrasive surface. Pad 220 has dimensions suitable for contacting localized areas of human skin. In one embodiment, pad 220 includes an abrasive surface. Such an abrasive surface may include a plurality of abrasive particles attached to a generally planar surface.

Pad 220 may be formed in/of a geometry desired. For example, in the embodiment illustrated in FIG. 1 and FIG. 2, pad 220 is suitable for rejuvenation treatments to the hand and feet of a human. It is appreciated that pad 220 and applicator 200 are also suitable for use on areas of skin besides hands and/or feet. Accordingly, pad 220 has, in this embodiment, geometry of a polygon shape such as the generally triangular shape shown in FIG. 1. The triangular shape allows pad 220 to be maneuvered between fingers and/or toes with a portion of the surface (e.g., an abrasive exterior surface) remaining in contact with the skin (e.g., at the base of a finger or toe). In one embodiment, each side 235 of triangular pad 220 has a length on the order of about 1.5 to four inches (3.5 to 10 cm). In one embodiment, each corner 230 of pad 220 is blunted reducing the distance to the corner by on the order of, for example, 0.01 to 0.67 inches (0.025 to 17 mm).

In the embodiment illustrated in FIG. 1, pad 220 includes exterior surface portion 255 (superior surface as viewed) that includes an abrasive surface. Pad 220 also includes body 265 a portion of which includes border 250 surrounding the abrasive surface. Border 250 may include a smooth, possibly deformable surface having a rounded edge.

Moreover, embodiments include pad 220 with a plurality of sides, such as side 235; a plurality of corners, such as corner 230; and a border, such as border 250. Embodiments include abrasive surfaces having a polygon shape including a plurality of elliptically shaped corners, each corner having two points where the elliptically shaped corner deviates from two sides of the polygon, and an apex. Moreover, each of those points may be located in a range of between 0.062 inches (1.5 mm) and 0.67 inches (17 mm) from where two sides of the polygon would meet to from an apex. Also considered, are abrasive surface geometries where a width of a rounded corner where the rounding of a polygon corner begins is in a range between 0.062 inches (1.5 mm) and 0.67 inches (17 mm) in width.

For instance, in the example shown in FIG. 1, generally triangular shaped pad 220 has three side lengths and three rounded corners, each corner comprising an elliptical shape having a curvature initiated along two side lengths of the triangle, where the curvature is initiated in the range between 0.1 inches (2.5 mm) and 0.67 (17 mm) inches from where the two side lengths, if continued, would form an apex. Note that although border 250 is shown in FIG. 1, embodiments considered include those with no border, and with various sufficient borders, such as borders having a width between the abrasive surface and the edge of pad 220 in the range of between 1 micrometer and 0.4 inches (1 centimeter).

Referring to FIG. 1 and FIG. 2, in one embodiment, an abrasive surface for pad 220 includes exterior surface portion 255 including an abrasive material layer of abrasive particles having a grit in the range between 40 and 200 grit. For example, an abrasive surface including grit in the range of approximately 30 grit to 100 grit can be used to remove a layer of human skin by abrading the skin when the applicator manipulates an epidermal layer of human skin to, for example, reduce the size of a callus, such as a callus on human skin, feet or hands. Moreover, such an embodiment can also be used to abrade a wart, corn, scar and rough skin.

In one embodiment, the abrasive surface of exterior surface portion 255 of pad 220 is similar to conventional sandpaper in that it has teeth and a gullet. The number of teeth per square inch represents a grit of the surface. The lower the number of the grit, the more abrasive is the surface. Furthermore, an abrasive surface may be either closed-coat (e.g., 90 percent or more of the abrasive surface is covered with abrasive particles) or open-coat (e.g., up to 90 percent, and conventionally 40 percent to 70 percent of the abrasive surface is covered with abrasive particles).

In one embodiment, exterior surface portion 255 of pad 220 includes abrasive particles on a backing such as a paper backing. Suitable abrasive particles representing particle grit include silicon carbide, aluminum oxide, ceramic, and garnet. Other materials include, but are not limited to, sand (e.g., silicon dioxide), metals, plastics and organic material. A backing of a generally planar surface may include one of a paper, a cloth, a metal and an organic material. In embodiments, abrasive particles may be attached to the backing by an appropriate means including by an adhesive, a cement, a paste, a gum, a glue, a resin and an epoxy. Exterior surface portion 255 is a portion of pad 220 or may be glued to other components of pad 220. Alternatively, exterior surface portions 255 may be removable from another component of pad 220 through, for example, a hook and loop type coupling.

Referring to FIG. 1 and FIG. 2, one embodiment of applicator 200 also includes pad 220 having cushioning layer 268 between, for example, an exterior surface and a cap component of applicator 200 (described below). In the embodiment shown in FIG. 2, pad 220 includes exterior surface portion 255 (such as an abrasive surface and backing), cushioning layer 260, and body 265 that acts as a frame and/or support for exterior surface portion 255 and cushioning layer 260. As illustrated, body 265 includes border 250 (described above). Suitable cushioning materials for cushioning layer 260 include various elastic material, padding material, such as foam, rubber, sponge, cork, plastic, gum and organic material. As such, cushioning layer 260 may allow an exterior surface of pad 220, such as an abrasive surface, to flex with the curvature of skin (e.g., a callus) that is applying pressure to the generally planar exterior surface.

Figure 4:
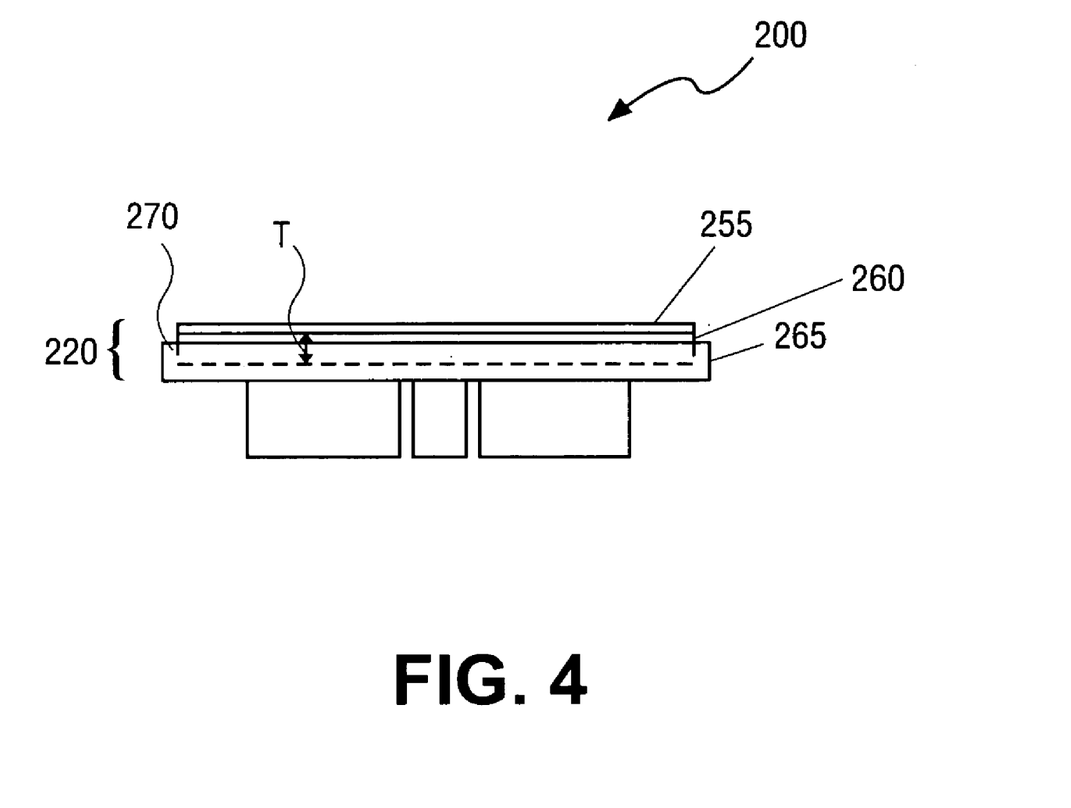
FIG. 4 is a schematic side view of the applicator of FIGS. 1–3.

According to an embodiment, body 265 may include a cavity to accept the cushioning layer. For example, FIG. 4 is a schematic side view of the applicator 200 of FIGS. 1–3. As shown in FIG. 4, applicator 200 includes pad 220 having cavity 270 formed in body 265 to define a volume in which a portion of cushioning layer 260 (all or a portion of cushioning layer 260) is disposed.

Embodiments include cushioning layers of various thickness. Suitable cushioning layer thickness, include a thickness in the range of between 0.01 inches (0.25 mm) and 0.5 inches (12.5 mm) in depth, T. Representatively, referring to FIG. 4, cushioning layer 25 may have a thickness in the range of between 0.06 inches (1.5 mm) and 0.12 inches (3 mm) in depth, T.

Figure 5:
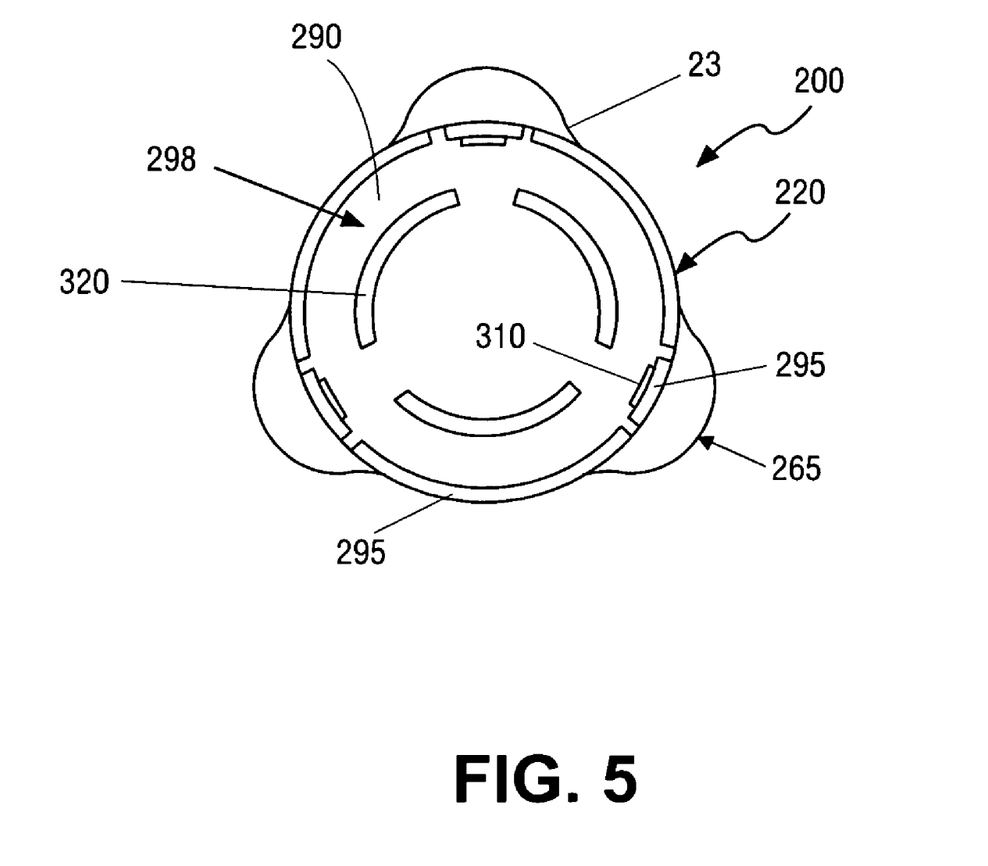
FIG. 5 is a schematic back view of an embodiment of applicator.

In addition to pad 220, applicator 200 includes cap 280. Cap 280 may be an integral part of a portion of pad 220 (e.g., such as integral with body 265 (e.g., integral plastic)) or affixed to pad 220. In the embodiment shown, cap 280 is integral with pad 220 so that a point of union of pad 220 and cap 280 constitutes an intermediate surface. Cap 280 also includes a sidewall extending longitudinally from the intermediate surface to define an interior volume 298 to accept a device, such as device or tool 110. For example, FIG. 5 is a schematic back view of an embodiment of applicator 200. FIG. 5 shows body 265 (of pad 220) and cap 280. Applicator 200 includes intermediate surface 290 and sidewall, such as sidewall 295, extending longitudinally from intermediate surface 24 to define interior volume 298 to accept a device, such as device or tool 110. Sidewall 295 is non-continuous in that it contains spaces or gaps to allow individual portions of sidewall 295 to flex independently. Suitable interior volumes (e.g., volume 298) for embodiments, include a volume having dimensions corresponding to dimensions of head portion of a device, such as head portion 140 of device 110, so that applicator 200 can be detachably connected to device or tool 110 such as by a threaded attachment, a pressure lift attachment, a "snap-on" attachment, and a hook and loop material coupling. Moreover, also contemplated are permanent couplings of applicators to devices.

Referring to FIG. 5 and sidewall 295 of cap 280, one embodiment further includes at least one protuberance 310 extending laterally from a portion of sidewall 295 into the interior volume so that applicator 200 may be detachably coupled to a device such as by snapping applicator 200 onto a head portion of a device to mount it thereon, and unsnapping applicator 200 from the head portion by a human hand.

Intermediate surface 290 and sidewall 295 may be made of various materials and have a range of sizes. Suitable intermediate surface and sidewall materials include plastic, metal, composite rubber and resin. One suitable range for a longitudinally extending length from the intermediate surface a distance in the range of from 0.06 inches (1.5 mm) to 0.67 inches (17 mm). Once determinate for a length of sidewall 295 is a length sufficient to engage or be engaged by a tool or device such as tool or device 110 (see FIG. 1 and FIG. 2). Likewise, suitable sizes or protuberances include protuberances extending longitudinally from a portion of the sidewall into the interior volume a distance in the range of between 0.01 inches (0.25 mm) and 0.25 inches (6.2 mm).

Cap 280 of applicator 220 may also include structure within the interior volume 298 such as ridges, tapered portions, protuberances, indexing structure, posts and recesses for receiving extensions of the device, in order to more firmly attach the applicator to the device. For example, as shown in FIG. 5, inner ridges 320 on intermediate surface 290 can be used to engage correspondingly shaped recesses in a head portion of a device so that applicator 200 is attached to the device more firmly and does not rotate or slide with respect to the head portion of the device.

Figure 6:
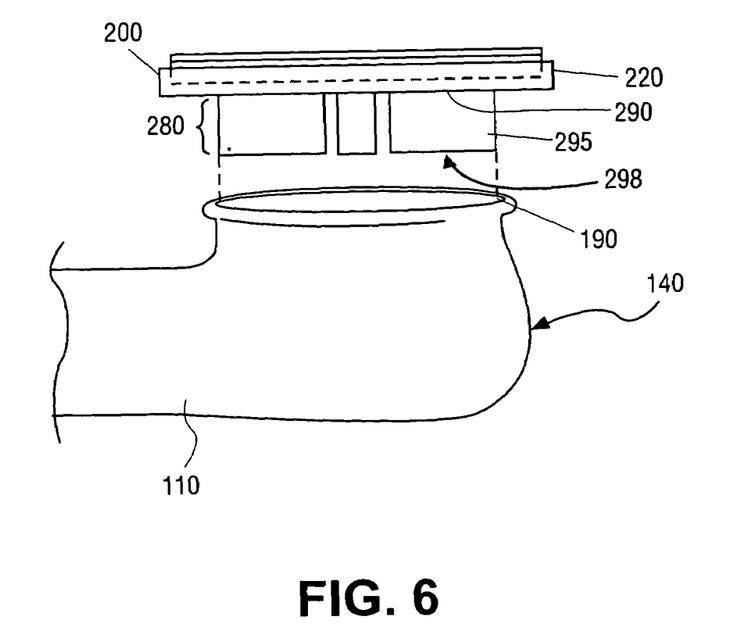
FIG. 6 shows an exploded, magnified side view of a portion of an apparatus illustrated in FIG. 1 and FIG. 2.
Figure 7:
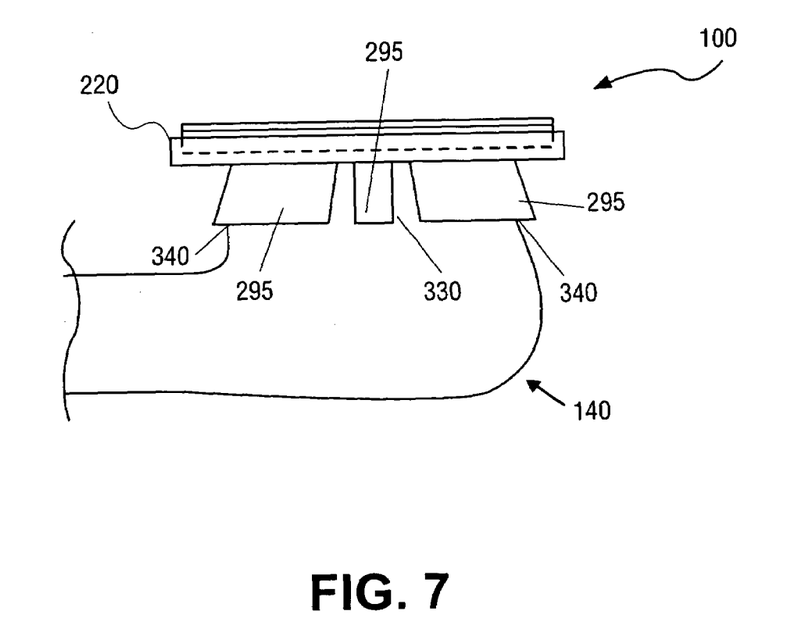
FIG. 7 shows a magnified view of a portion of apparatus.

FIG. 6 shows an exploded, magnified side view of a portion of apparatus 100 illustrated in FIG. 1 and FIG. 2. FIG. 7 shows a magnified view of a portion of apparatus 100. Illustrated in FIG. 6 and FIG. 7 is a portion of device or tool 110 and applicator 200. FIG. 6 shows the configuration of applicator 200 to head portion 140 of device or tool 110. In one embodiment, applicator 200 is connected to head portion 110 through cap 280. As noted above, with respect to FIG. 4 and FIG. 5 and the accompanying text, cap 280 includes intermediate surface 290 and sidewall 295 extending longitudinally from intermediate surface 290. Sidewall 295, as illustrated, is a circular body having a diameter similar to a diameter (also circular in one embodiment) of head portion 140 of device or tool 110. In one embodiment, head portion 140 has a diameter on the order of about one to two inches (about 2.5 to 5 centimeters). In one embodiment, a diameter of a portion of head portion 140 (represented by lip 190) is slightly larger on the order of, for example, 0.01 to 0.03 inches (one to two millimeters) than a main body of head portion 140.

Intermediate surface 290 and sidewall 295 define interior volume 298 of cap 280. One or more laterally extending protuberances 310 (See FIG. 5) extend from sidewall 295 into interior volume 298 to reduce a diameter of the interior volume (when measured across one or more protuberances 310). In this manner, cap 280 does not fit easily over lip 190 of head portion 140. In one embodiment, sidewall 295 is made of a thin plastic material that allows sidewall 295 to be deformed and depressed on (snapped) over lip 190 onto head portion 140 of device or tool 110. In one embodiment, cap 280 is depressed on head portion 140 of device or tool 110 so that one or more protuberances 310 are positioned inferior to lip 190 (as viewed in the orientation of FIG. 6).

FIG. 7 shows applicator 200 mounted over a portion of head portion 140 through volume 298. Thus applicator 200 is detachably coupled to apparatus 110 and sidewalls 295 are shown slightly flexed outward and slots 330 are wider toward device or tool 110 so that sidewalls 295 can expand to tightly fit over a portion of head 140 at location 340. In this embodiment, portion of sidewall 295 of applicator 200 having protuberance 310 may be snapped onto head portion 140 snapping over a lip 190 to form a "snap-on" detachable coupling of applicator 140 to apparatus 110.

Applicator 200, which may be secured to head portion 140 of device or tool 110 may be replaced after one or many uses. In one embodiment, applicator 200 may be removed from the device or tool 110 after use and cleaned. When it is considered to be no longer useful after, for example, one or more cleanings, applicator 200 may be discarded and replaced.

It is believed that in applying a composition such as described above to an area of human skin and manipulating the composition with an apparatus, such as apparatus 100 (e.g., buffing the skin), as the vibrating action of the apparatus (e.g., of the applicator) helps stimulate skin, muscle, and tissue to revitalize the treated area. It is appreciated that, in use, the vibrating mechanism may or may not be used.

It is also contemplated to buff the skin with a mechanism capable of rotating or spinning the applicator either in place of or in conjunction with the vibrating motion described above. In an embodiment, the spinning mechanism is configured to spin the applicator about a central axis of the applicator. In another embodiment, the spinning mechanism is configured to spin the applicator about an off-center axis of the applicator (e.g., to produce a random orbit). A representative random or standard orbit oscillation is on the order of 6,000 or fewer revolutions per minute. One such configuration would allow an applicator such as applicator 200 to be coupled to a shaft of a motor (motor 160 in FIG. 3).

In addition, various embodiments include a sonic wave generator disposed either within the applicator, adjacent thereto, or both. In operation, sonic waves created by the sonic wave generator travel through the applicator and massage the skin of the user. One suitable sonic wave generator is an ultrasound generator that generates sound waves from, for example, a vibrating crystal in a generator. The sound waves may be used to increase circulation to an area being treated.

Figure 8:
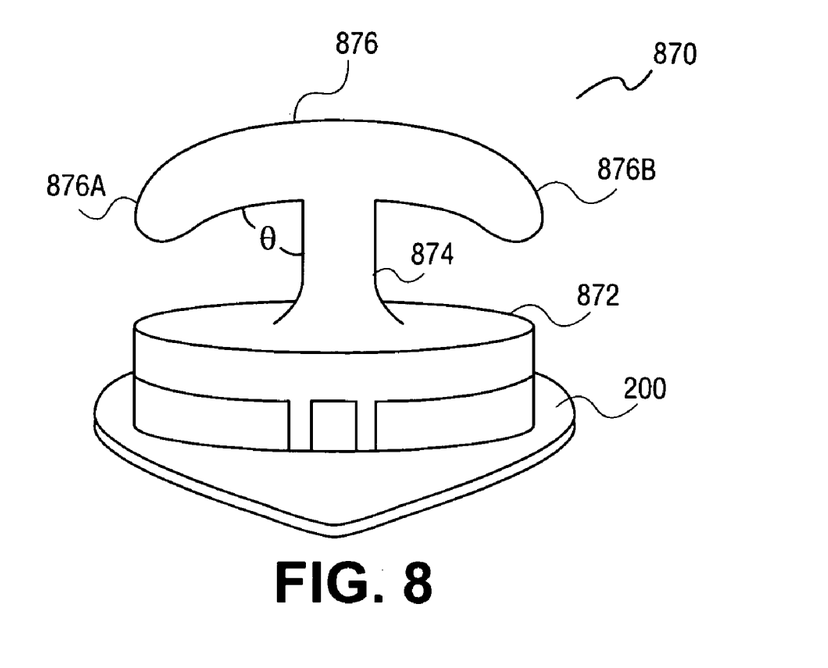
FIG. 8 is a schematic side view of an embodiment of a device for gripping by a human hand.

FIG. 8 is a schematic side view of an embodiment of a device for gripping by a human hand having an applicator. FIG. 8 shows an embodiment of a manually-manipulated apparatus. Apparatus 870 includes head portion 872 and a handle portion coupled to the head portion and suitable for gripping by a human hand. The handle portion includes first member 874 extending from head portion 872 and second member 876 coupled to first member 874 at an angle (θ). Angle θ is between 0 and 180 degrees. Second member 876 has first end 876A, second end 876B, and an intermediate portion between first end 876A and second end 876B. Applicator 200 is coupled to head portion 872 and has dimensions suitable for contacting localized areas of human skin.

The shape of the handle portion allows a user to grip the apparatus in different fashions to facilitate application of a suitable composition, as described herein. For example, a user can slide their fingers under second member 876 so that a palm of the user is facing down towards head portion 872. Alternatively, a user can grasp second member 876 with their fingers.

Figure 9:
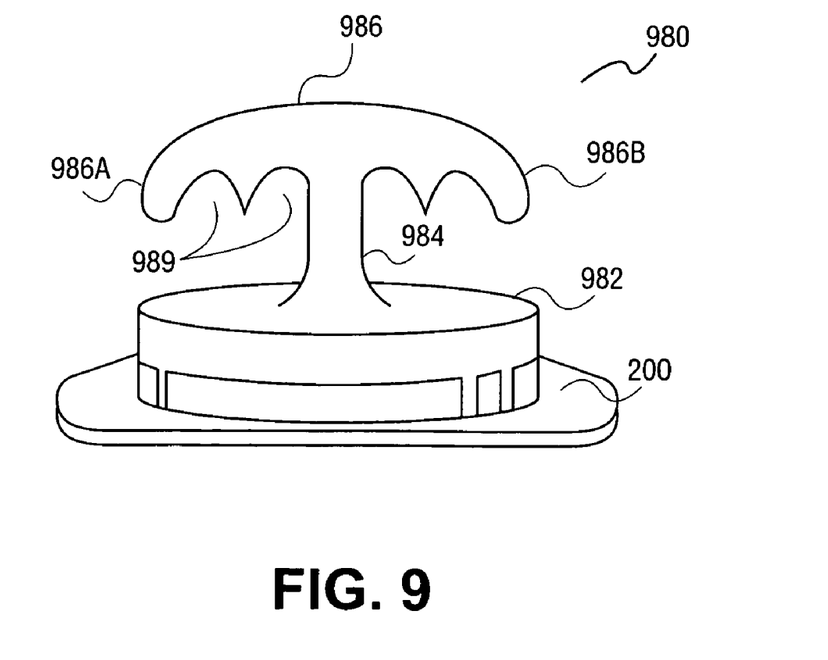
FIG. 9 is a schematic side view of an embodiment of a device for gripping by a human hand.

FIG. 9 is a schematic side view of an embodiment of a device for gripping by a human hand. FIG. 9 shows an embodiment of a manually-manipulated apparatus. Apparatus 980 includes head portion 982 and a handle portion coupled to the head portion and suitable for gripping by a human hand. The handle portion includes first member 984 extending from head portion 982 and second member 986 coupled to first member 984. Applicator 200 is coupled to head portion 982 and has dimensions suitable for contacting localized areas of human skin.

Second member 986 has first end 986A, second end 986B, and an intermediate portion between first end 986A and second end 986B. The intermediate portion of second member 986 is coupled to first member 984. In addition, the intermediate portion of second member 986 has grooves 989 formed therein. Each groove 989 can accommodate at least one human finger. Although grooves 989 are disposed on the underside of second member 986 in FIG. 9B, grooves 989 may be placed in any orientation and/or location on second member 986 to facilitate handling by a user.

Figure 10:
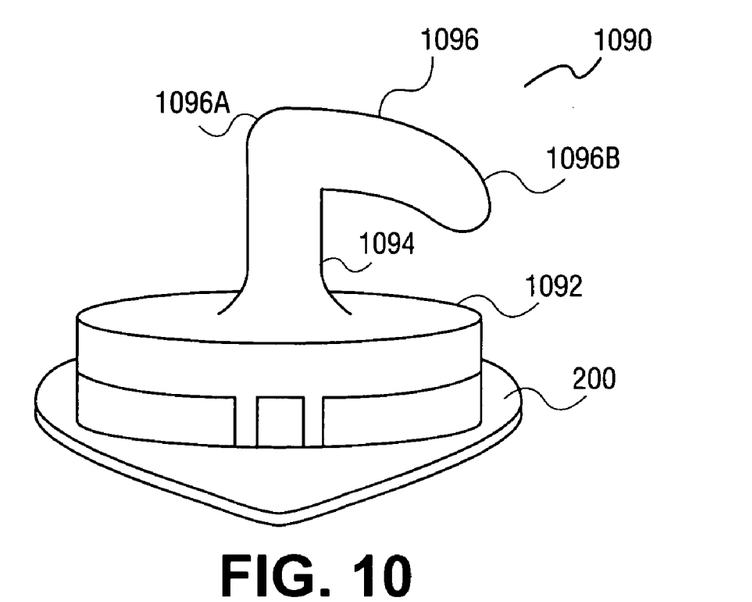
FIG. 10 is a schematic side view of an embodiment of a device for gripping by a human hand.

FIG. 10 is a schematic side view of an embodiment of a device for gripping by a human hand. FIG. 10 shows an embodiment of a manually-manipulated apparatus. Apparatus 1090 includes head portion 1092 and a handle portion coupled to the head portion and suitable for gripping by a human hand. The handle portion includes first member 1094 extending from head portion 1092 and second member 1096 coupled to first member 1094. Applicator 200 is coupled to head portion 1092 and has dimensions suitable for contacting localized areas of human skin.

Second member 1096 has first end 1096A, second end 1096B, and an intermediate portion between first end 1096A and second end 1096B. First end 1096A of second member 1096 is coupled to first member 1094.

Figure 11:
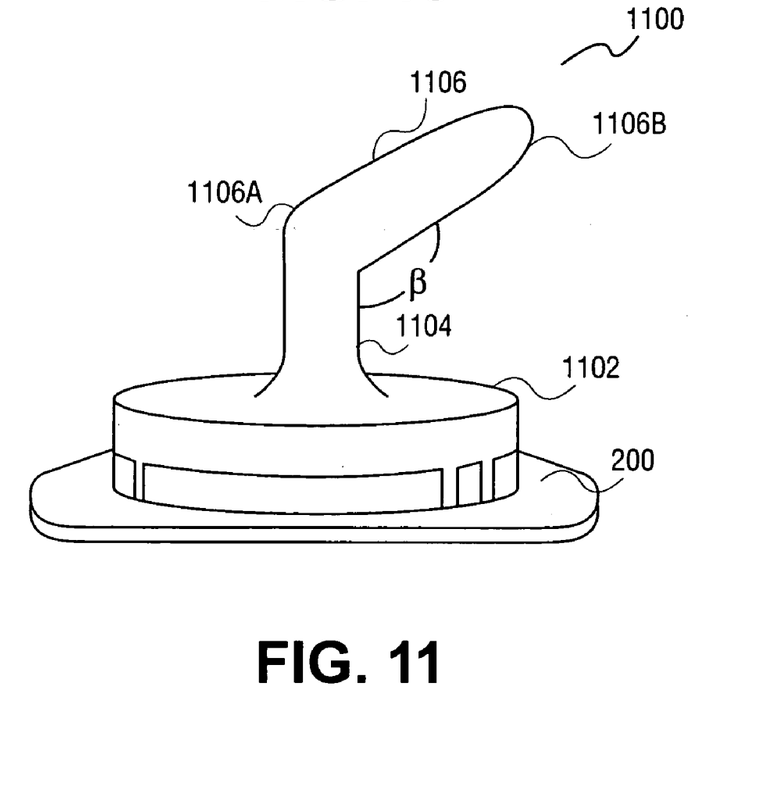
FIG. 11 is a schematic side view of an embodiment of a device for gripping by a human hand.

FIG. 11 is a schematic side view of an embodiment of a device for gripping by a human hand. FIG. 11 shows an embodiment of a manually-manipulated apparatus. Apparatus 1100 includes head portion 1102 and a handle portion coupled to the head portion and suitable for gripping by a human hand. The handle portion includes first member 1104 extending from head portion 1102 and second member 1106 coupled to first member 1104. Applicator 110 is coupled to head portion 1102 and has dimensions suitable for contacting localized areas of human skin.

Second member 1106 has first end 1106A, second end 1106B, and an intermediate portion between first end 1106A and second end 1106B. First end 1106A of second member 1106 is coupled to first member 1104 at an angle (β). In the embodiment shown, β is an obtuse angle. In embodiments, as shown in FIGS. 8–11, applicator 200 may be coupled to the head portion of the manually-manipulated apparatus such as by means or structures as described above with respect to FIGS. 1–7.

Embodiments include a method of manipulating an applicator over an area of human skin with an apparatus having a handle portion coupled to a head portion and suitable for gripping by a human hand. Thus, a layer of human skin can be reconditioned or removed by applying, for example, an abrasive composition and/or the abrasive surface apparatus to human skin and manipulating the composition and/or abrasive surface on the human skin to allow the abrasive surface to abrade a epidermal layer of the human skin. With the use of an apparatus such manipulating of the applicator can include vibrating the apparatus, spinning the apparatus and propagating sonic waves through the apparatus.

Moreover, embodiments include applying a composition to an area of human skin that an apparatus is to be manipulated over. Suitable compositions include those described above. Thus, a suitable composition can be applied between the abrasive surface and the area of skin to be treated, such as by applying the composition directly to the area of skin, or to the abrasive surface prior to manipulating an apparatus over the area of skin.

Figure 12:
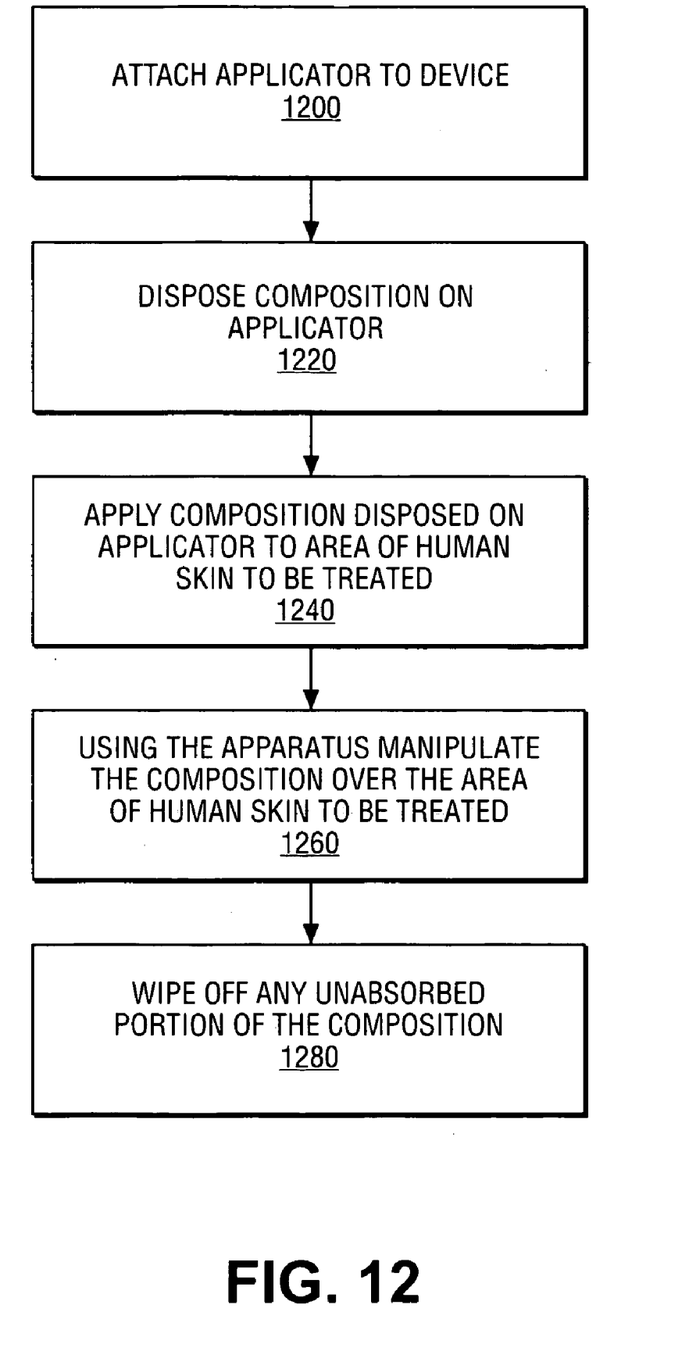
FIG. 12 is a flow chart describing one embodiment of an operation to treat skin

For example, FIG. 12 is a flow chart describing one embodiment of an operation to human skin. FIG. 12 shows a flow chart illustrating, for example, a method utilizing either the apparatus comprising the motor-driven device (e.g., device or tool 110 in FIGS. 1–3) or the manually-manipulated device (e.g., devices 870, 980, 1090 and 1100 in FIGS. 8–11). Initially, a human user attaches an applicator to the device (e.g., manual device or motion generated vibrator or random orbit motion apparatus) (block 1200). Next, the composition of, for example, moisturizer and abrasive particles, can be disposed on the applicator (block 1220). This can be accomplished either by dipping the applicator into a container with the composition disposed inside or by disposing the composition directly onto the applicator (e.g., with a dispenser, a squirt bottle tube, spatula or other suitable means).

The user then applies the composition disposed on the applicator to the area of skin to be treated (block 1240). One example is applying approximately one-quarter inch of the composition across the entire surface of a porous applicator.

The user then dots the area to be treated at locations on the order of, for example, three inches apart.

Subsequently, the user manipulates the composition over the area of skin to be treated with the apparatus (vibrator) (block 1260). In an embodiment, manipulation of the composition (block 1260) is characterized by moving the apparatus (e.g., manual device or motion generated vibrator or random orbit motion apparatus) over the area of skin using firm, upward, circular strokes. In one example, the manipulation of the composition is continued for one to ten minutes or until the composition has been worked into the skin and the skin appears soft and smooth. In another example, a user manipulates the apparatus to softening calluses by manipulating the applicator by hand or with a motorized device, as described above, on damp or dry skin to minimize any rough skin areas (including extremely rough and thick calluses) such as heals, feet or cuticles. More particularly, a composition, such as an embodiment described above can be applied to clean dry skin using the applicator. With respect to rejuvenating hands and/or feet, such uses may include applying a firm gentle pressure and moving the applicator across the hands and feet using slight upward circular motions for one to five minutes per area.

Finally, the user wipes off any unabsorbed portion of the composition (block 1280) and may optionally rinse or cleanse the area. In one embodiment, the composition including a moisturizer as a principal component may be worked in until substantially all of the moisturizer (and any other components) is taken up by the skin and only the abrasive particles remain on the surface of the skin. The abrasive particles may be brushed off and the area of skin cleansed with a mild cleanser. In an alternative embodiment, before applying the composition to the skin, the user cleanses the area of skin with a mild cleanser using gentle circular strokes, rinses the skin with tepid water, and pat the skin dry with a soft towel.

It should be noted that in applying the composition to the skin, the user may dab the composition on certain areas of the skin before switching the apparatus (vibrator) on to manipulate the composition over the skin. Alternatively, the user may simultaneously apply the composition to the skin and manipulate the composition over the area of skin to be treated. Alternatively, the user may simultaneously apply the composition to the applicator, dot the area to be treated and manipulate in rotary strokes. Using the vibrator applicator, the user may manipulate the applicator with the vibrator in the on (vibrate) position, or in the off position for a lighter treatment.

The above described method described a rejuvenation treatment involving both a composition and an apparatus (tool and applicator). It is appreciated that either the composition or the apparatus may be used alone in connection with rejuvenation treatments. For example, embodiments of the composition may be applied and manipulated by hand or with a wash cloth. An apparatus including an applicator having an abrasive surface may be used with or without a composition including water.

It is to be understood that even though numerous characteristics and advantages of various embodiments have been set forth in the foregoing description, together with details of structure, function, and formulations of the various embodiments, this disclosure is illustrative only. Changes may be made in detail, especially matters of structure, management of parts, and compositional formulation, without departing from the scope of the various embodiments as expressed by the broad general meaning of the terms of the appended claims.

What is claimed is:

1. A composition suitable for application to human skin comprising:
   a base comprising, in an amount greater than one weight percent of the composition, at least one component that has a property of a moisturizer that attracts moisture to a top skin layer; and
   a plurality of abrasive particles having an average particle size of about 100 micrometers to about 556 micrometers suspended in the base.

2. The composition of claim 1, further comprising:
   one of a vitamin, a mineral, an antioxidant, a cleanser, and an emulsifier.

3. The composition of claim 1, further comprising one of a moisturizer liquid, a moisturizer gel, and a moisturizer emollient.

4. The composition of claim 3, wherein the plurality of abrasive particles comprises one of corundum, magnesium oxide, and a precious stone suspended in the moisturizer.

5. The composition of claim 4, wherein the precious stone comprises one of diamond, garnet, sapphire, ruby, emerald, and topaz.

6. The composition of claim 1, wherein the abrasive particles comprise a dimension suitable to remove a hair from or smooth a callus on a skin of a hand or foot of a human subject without damaging the skin.

7. The composition of claim 1, wherein the composition includes corundum, Vitamin A, Vitamin C, and Vitamin E.

8. A composition suitable for application to human skin comprising:
   a base including a percentage by weight of water between 20 percent by weight and 50 percent by weight, a percentage by weight of caprylic between 3.5 percent by weight and 15 percent by weight, and a percentage by weight of ethylhexyl palmitate between 3.9 percent by weight and 12 percent by weight; and
   a plurality of abrasive particles having an average particle size of about 100 micrometers to about 556 micrometers suspended in the base.

9. The composition of claim 8, further comprising one of a percentage by weight of safflower seed oil between 3 percent by weight and 10 percent by weight; a percentage by weight of glycerin between 1.9 percent by weight and 5 percent by weight; a percentage by weight of shea butter between 0.9 percent by weight and 3 percent by weight; and a percentage by weight of jojoba oil between 0.9 percent by weight and 3 percent by weight.

10. The composition of claim 8, wherein the plurality of abrasive particles comprises one of diamond, garnet sapphire, ruby, emerald, and topaz suspended in a moisturizer.

11. The composition of claim 8, wherein the plurality of abrasive particles comprises one of silicon carbide, silicon carbide coated particles, and magnesium oxide.

12. The composition of claim 8, wherein the plurality of abrasive particles comprises one of corundum, aluminum oxide, and alumina.

13. A composition suitable for application to human skin comprising:
   a base comprising, in an amount greater than one weight percent of the composition, at least one component that has a property of a moisturizer that attracts moisture to a top skin layer; and
   a plurality of corundum crystals having a mesh size of 100 mesh (large) in a 30 percent to 75 percent by weight concentration suspended in the base.

14. The composition of claim 13, further comprising a percentage by weight of safflower seed oil between 3 percent by weight and 10 percent by weight; a percentage by weight of glycerin between 1.9 percent by weight and 5 percent by weight; a percentage by weight of shea butter between 0.9 percent by weight and 3 percent by weight; and a percentage by weight of jojoba oil between 0.9 percent by weight and 3 percent by weight.

15. The composition of claim 13, wherein the base comprises one of a soap, a salicylic acid, a sodium lauryl sulfate, and a sodium laureth sulfate.

16. The composition of claim 13, further comprising a safflower extract, a wheat germ extract, a carrot extract, a *calendula* extract, and an aloe extract.

17. The composition of claim 13, further comprising peppermint oil and rose oil.

18. The composition of claim 13, further comprising one of a moisturizer liquid, a moisturizer gel, and a moisturizer emollient.

19. The composition of claim 18, further comprising a surfactant and an emulsifier.

20. The composition of claim 13, wherein the at least one component comprises one of glycerin, propylene glycol, alpha hydroxy acid, urea, and lactic acid.

21. The composition of claim 13, wherein the at least one component comprises one of glycerin, propylene glycol, alpha hydroxy add, urea, and lactic add.

22. A composition suitable for application to human skin comprising:
- a base wherein the base comprises a percentage by weight of aloe gel between 5 percent by weight and 75 percent by weight and a percentage by weight of sodium lauryl sulfate between 5 percent by weight and 20 percent by weight; and
- a plurality of corundum crystals having a mesh size of 100 mesh (large) in a 30 percent to 75 percent by weight concentration suspended in the base.

* * * * *

UNITED STATES PATENT AND TRADEMARK OFFICE
CERTIFICATE OF CORRECTION

PATENT NO. : 7,179,152 B1 Page 1 of 1
APPLICATION NO. : 10/359852
DATED : February 20, 2007
INVENTOR(S) : Rhoades

It is certified that error appears in the above-identified patent and that said Letters Patent is hereby corrected as shown below:

In Claim #21, Line #3, please delete "add," and insert -- acid, --.

In Claim #21, Line #3, please delete "add." and insert -- acid. --.

Signed and Sealed this

Fourteenth Day of August, 2007

JON W. DUDAS
*Director of the United States Patent and Trademark Office*